United States Patent [19]

Lord

[11] Patent Number: 5,525,061
[45] Date of Patent: Jun. 11, 1996

[54] COORDINATION TESTING APPARATUS

[76] Inventor: William P. Lord, 50 Kennedy Dr., Keene, N.H. 03431

[21] Appl. No.: 287,777

[22] Filed: Aug. 9, 1994

[51] Int. Cl.⁶ .................................... G09B 9/00
[52] U.S. Cl. .................. 434/258; 434/354; 434/367
[58] Field of Search .................... 434/258, 260, 434/326, 354, 363; 128/774; 364/413.02

[56] References Cited

U.S. PATENT DOCUMENTS

| | | | |
|---|---|---|---|
| 3,046,676 | 3/1960 | Hermann et al. | 434/258 |
| 3,357,115 | 4/1966 | Kelley . | |
| 3,690,020 | 9/1972 | McBrantie | 35/37 |
| 3,869,812 | 3/1975 | Arakelian et al. | 434/258 |
| 4,325,697 | 4/1982 | Regan et al. | 434/258 |
| 4,885,687 | 12/1989 | Carey | 434/258 |

*Primary Examiner*—John S. Hilten
*Attorney, Agent, or Firm*—George W. Dishong

[57] ABSTRACT

A method and apparatus for testing and evaluation of physical coordination and dexterity in occupational rehabilitation or physical therapy for injury or illness, and for training of retarded or developmentally delayed or handicapped persons. The person being tested attempts to traverse a test pattern with a targeting image or to plot coordinates and connect line segments from instructions, using left and right hands or feet to control motion or plot coordinates in at least two dimensions. Controls can be oriented and configured to test and train motor skills, motions and coordination requirements common to workplace, home or recreational activities. A permanent trace record of the subject's effort, made in the same orientation and scale as the test pattern, provides a means by which test results can be compared directly to the test standard, to previous and later recorded traces by the same subject, and to the traces of other subjects.

7 Claims, 6 Drawing Sheets

COORDINATION TESTING APPARATUS

BACKGROUND OF THE INVENTION

1. Field of the Invention

This invention most generally relates to the training, testing and evaluation of coordination in occupational rehabilitation or physical therapy for injury or illness, and for training, testing and evaluation of retarded or developmentally delayed or handicapped persons.

More particularly, this invention relates to exercising and measuring dexterity and coordinated use of the bilateral upper extremities.

More particularly yet, the invention relates to the rehabilitation of children and adults in the areas of functional training and restoration of hand fine motor coordination in conjunction with gross motor work at the wrist, forearm and shoulder. Secondarily, it relates to use in pediatric work to teach and improve fine and gross motor coordination while increasing attention span.

Even more particularly, the invention relates to aiding and evaluating individuals disabled by orthopedic injuries of the upper extremity such as fractures, arthritides, peripheral nerve injuries, reflex sympathic dystrophy, bronchial plexus injuries and related post operative diagnosis and treatment programs.

Yet even more particularly, the invention relates to encouraging and improving the coordinated use of finger and thumb opposition, metacarpal adduction and abduction, finger flexion and extension, and individual wrist movements and combinations of same, forearm supination and pronation, and movements that change shoulder joint position to appropriately position the arms for functional hand use.

The invention further relates to treatment for individuals with diagnosis of brain injury or diseases, central nervous system disorders, and retraining of individual upper extremity and trunk patterning, relearning or teaching spatial concepts, right/left coordination of differentiation, ability to follow directions, recognition and/or retraining of field of vision deficits and other cognitive functions.

The invention yet further relates to the testing and development of the functional use of upper extremities in combinations of motions, in both standing and sitting positions, and to the simulation of hand/eye coordination and motion of work station functions such as the operative functions of a machine tool, as applicable to work hardening and industrial rehabilitation programs.

The invention still yet further relates to the specific machines, devices, methods and procedures for testing and treatment of the above-cited problems and circumstances, and for recording and comparing the results.

2. Description of the Prior Art

The broad problem not resolved by the prior art is the lack of a coordination training, testing and evaluation method and apparatus that contemplates a simple, inexpensive, easily administered test procedure combined with readily configurable, two-handed input controls that can be closely configured to simulate the types of movements, range of motions and dexterity normally required or expected in the workplace or other common environments of the person tested. Additionally there is a lack of a simple, inexpensive method of recording a standardized form of the results of such testing for easy comparison to testing standards, to previous and later tests by the same individual, and to the results of other tested subjects.

U.S. Pat. No. 4,885,687, Carey, Dec. 5, 1989, introduces the measurement of the force and angle applied by the subject to control and coordinate a trace in response to a variety of master patterns. This disclosure illustrates a one-handed pistol grip style input with no suggested or apparent flexibility of configuration, resulting in a test capability of narrow scope and limited use.

U.S. Pat. No. 4,325,697, Regan et al., Apr. 20, 1982, discloses a multitude of channels of visual perception and awareness, to include sensitivity to the changing size of a test image. The testing method and device is directed to the subject's ability to track changing sizes of the master pattern, a rectangle being the preferred image. Flicker and lateral motion are mentioned, as well. Analytical schemes for testing and measuring deviations are discussed. The matter of the subject's manual entry of control inputs is trivialized to mention of a control knob, with no suggestion or hint that the nature of the required physical, functional response might be meaningful.

U.S. Pat. No. 4,589,849, Casey, May 20, 1986, is a task specific testing and training device that by design tests the specific, result-oriented skill set required to insert components on a printed circuit boards, by evaluating the resulting "product". There is no consideration or differentiation of handedness or of the detailed coordination of digits, palm, wrist, forearm, upper arm and shoulder motion and flexibility required for control inputs. It is basically a very specific result-focused, job screening device.

U.S. Pat. No. 5,158,303, Lat, Oct. 27, 1992, discloses a handle and "eye" on a wire track, which handle and "eye" the testee attempts to pass over the length of the wire without contacting the wire before a timer expires. While technically a hand and eye coordination testing device, it is more reminiscent of a carnival game, and makes no contribution alone or in combination to the problem addressed herein by this applicant.

The applicant knows of no prior art, alone or in combination, that discloses or leads to the very significant features and advantages of the present invention.

SUMMARY OF THE INVENTION

The main purpose of the invention is to provide a clinical and industrial tool with broad application for the training, retraining, testing and evaluation of persons whose physical strength, range of motion, coordination, and dexterity in the context of the functional requirements of common workplace, home or recreational activities, is of concern.

The invention in its simplest form is a method and corresponding apparatus suitable for configuring left and right control inputs to simulate the desired motions and movements to be tested, presenting a visual test pattern to the person to be tested, presenting a targeting image superimposed over the test pattern, having the person being tested, either sitting or standing, traverse or negotiate the test pattern by controlling the relative position and movement of the targeting image with respect to the test pattern by operating or manipulating the left and right input controls in harmony, the apparatus concurrently making a permanent trace of the control inputs of the person being tested for comparison to the test pattern.

An alternate and additional purpose and capability of the basic invention is to present instructions for coordinates and connecting line segments to the person being tested which are then plotted by referencing a scale and pointer in each dimension and by using the same left and right control inputs described above.

A primary object of the invention is to provide for great flexibility in the configuration of the left and right control inputs which includes hand-operated left and right rotatable shafts that can be oriented as front, side or top facing shafts, the choice of which allows for testing of different combinations of upper body, shoulder, arm, wrist and hand motion and coordination, and left/right differentiation. Examples of various input shaft orientations are further illustrated in the drawings.

Another primary object of the invention is to provide a variety of grip styles to further expand the flexibility of the input controls in order to focus on and test specific functional combinations of motions, coordination and gripping dexterity. Such various and useful grip styles include knob handles, "T" or "T bar" handles, pin handles, crank handles, and rim handles; each of which requires a somewhat different skill set of muscle and motion coordination and dexterity. Examples of these grip styles are illustrated in the drawings.

An additional object of the invention is to provide a simple, objective test pattern that is made up of transverse and vertical line components which may be connected in continuous line segments, the result of which is an unambiguous test pattern for the person being tested to follow with alternating left and right inputs while proceeding through the test. A clear standard of this sort contributes to the objectivity and clinical usefulness of evaluations of left and right side differentiation in addition to other aspects of test.

A further objective of the invention is to provide for adjustable amounts of resistance in the input controls in order to increase or decrease the control effort required of the person being tested.

A yet further objective of the invention is to provide for adjustable or selectable turn ratios between the input shafts and the resultant motion of the targeting image in order to increase or decrease the range and content of motion and dexterity required of the person being tested.

A still yet further objective of the invention is to make or provide a permanent trace or record of the effort of the person being tested in the same orientation and scale as the test pattern, so that the trace can be directly compared to the test pattern for a raw score, to past and future traces by the same person for indications of improving or deteriorating performance, and to the traces of other persons for comparison to peers or average results of others.

Yet another objective of the invention is to provide a drum rotatable in either direction on a horizontal axis in front of the person being tested, on the right side of which can be attached in uniform registration a test pattern, over which test pattern is suspended a substantially transparent targeting image of cross hairs or equivalent sight picture or aiming devise, control of the relative position of the targeting image on the test pattern being caused by rotating a right hand input to rotate the drum and test pattern beneath the targeting image in either direction in a vertical dimension and by rotating a left hand input to slide the targeting image across the test pattern in either direction in a transverse dimension. Additionally, the invention should provide for attaching a blank trace record in uniform registration on the left side of the drum and a marker supported by a stylus sector arm in marking contact with the trace record such that the drum rotates beneath the marker the same amount in the same direction as beneath the targeting image, and the marker being mechanically linked to the targeting image such that transverse motion of the targeting image causes the marker to move the same distance in the same direction, thus making a permanent trace of the control inputs of the person being tested in the same orientation and scale as the master pattern.

Still yet another object of the invention is to provide for scales and pointers for plotting coordinates in at least two dimensions and connecting them with line segments, such as a transverse index scale pointer attached to the targeting image and a transverse index scale attached in a fixed position on the apparatus in front of the drum so that the transverse component of a coordinate can be selected by moving the pointer with right hand inputs to the correct location on the transverse index scale, and such as a vertical index scale on the right side of the drum that rotates beneath or near a vertical index scale pointer attached to the right side of the apparatus so that the vertical component of a coordinate can be selected by moving the vertical index scale and drum with left hand inputs to position the pointer at the correct location on the vertical index scale, the marker and sector arm being rotatable up and back to be effectively on or off for creating connecting line segments between the coordinates.

DESCRIPTION OF THE PREFERRED EMBODIMENT

To those skilled in the art, the invention admits of many variations in both method and apparatus, and in the applications thereof.

For example, the method and apparatus may be used for but are not limited to training, testing and evaluation of physical coordination in occupational rehabilitation or physical therapy for injury or illness, and for training and testing of retarded or developmentally handicapped persons. The invention may be practiced in either a standing or sitting position. While the intention of the design is to enable coordination training and testing using both left and right side inputs together, primarily using both hands, it is also applicable to one-handed use, or adaptable to use with one's feet.

As another example, the means of presentation of the test pattern or other instructions to the testing person may be embodied in an apparatus with an electronic, mechanical or other type display, either integral or separate from the control inputs and the trace output device. In mechanical displays, the test pattern may be displayed on a planar surface overwhich a targeting image is suspended and movable in two dimensions in a plane parallel to that of the test pattern. Alternatively, the test pattern may be displayed on a belt suspended on two or more drums such that all or a portion of the test pattern is presented in a planar form, but is movable in at least one dimension by rotation of the drums and resultant travel of the belt.

As yet another example, printed test patterns may be in the form of transverse and vertical line components connected into continuous line segments, or in the form of a "connect the dots" pattern in a lettered or numbered sequence. Additionally, test patterns may contain a predominantly transverse or vertical parallel line pattern, combined with a selected input control configuration, which requires a preponderance of a particular form of input control in order to exercise and test the particular motion of interest. In the case of instructions for plotting coordinates and creating connecting line segments and similar testing techniques, graphic or written instructions, live voice instructions or audio tapes may be used.

As still yet another example, the left and right manual control inputs required by the invention may be embodied in an apparatus which converts mechanically, electrically, electronically or by other means or combination of means, either integrally or separately from the presentation means and the trace maker output means.

As a further example, the trace maker may function mechanically, electrically, electronically, or by other means or combination of means, either integrally or separately from the presentation means and the manual control inputs.

As a yet further example, the testing can be time limited, so that the degree of completion within the time limit becomes another factor or basis for evaluation.

As another further example, controls can be oriented and configured to test and train motor skills, motions and dexterity common to workplace requirements or domestic and recreational environments.

As yet another further example, left and right control inputs may be defined to require only force or torque without significant motion, or may require a measurable amount of motion or displacement, and may incorporate a selectable or predetermined resistance to applied forces.

As an additional example, where rotational control input motions are difficult or not relevant, the subject can use non-rotational control inputs with either hands or feet, for example by using feet to apply alternating pressure or movement from neutral to heel or to toe and back to neutral, motion analogous to a using a two-way switch, thereby providing a sufficient number of input combinations to yield the two-way vertical motion and two-way transverse motion required of the preferred embodiment of the invention.

As another additional example, the method, where the apparatus is an electronic or holographic or other actual or simulated three dimensional display means, and where the control inputs are modified to provide two additional signals for plus and minus motion in a third dimension, easily accommodates a three dimensional format.

As yet another additional example, a permanent trace or record of the subject's effort made in the same orientation and scale as the test patterns or master pattern of the instructions provides a means by which coordination can be compared directly to the standard, to previous and later recorded traces by the same subject, and to the traces of other subjects.

The following is merely a description of the preferred embodiment of the invention. In this embodiment, a base plate supports left and right side plates to which are secured a front plate and deck plate, thus forming a storage area for accessories in the middle of the apparatus. A carrying handle is secured to the front plate for convenience, although the unit may be stored and transported in a suitable case.

Left and right side panels extend out and downward, secured to the side plates and the base. The side panels have slots for the left and right side rotatable input shafts.

Left and right front rotatable input shafts are located at the respective left and right sides of the front plate.

Figures 2, 3, 4A, 4B, 4C, 4D, 4E:
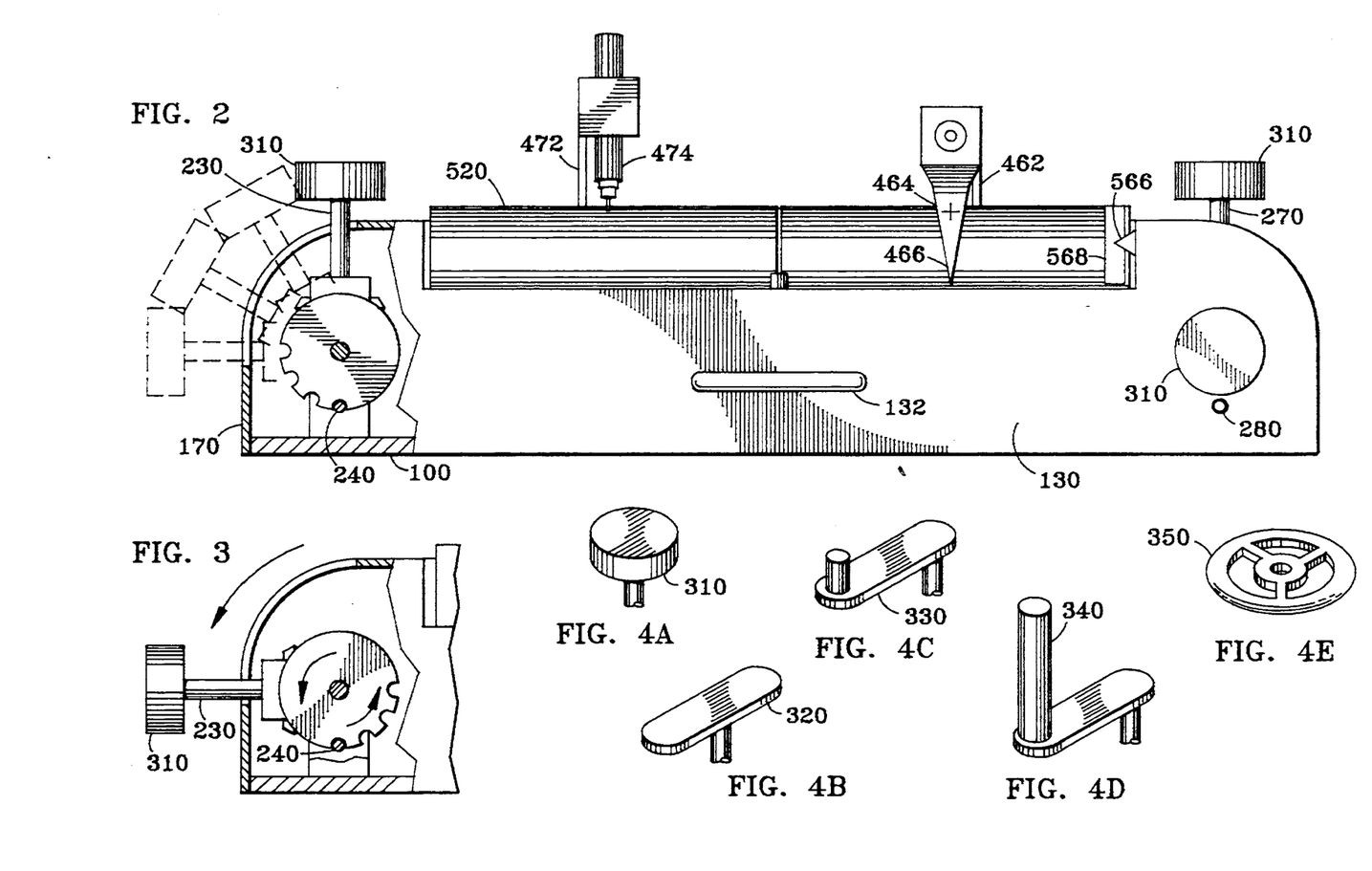
FIG. 2 is a front elevation with a partial cut-away view of the left-side input shaft and left side gear box, showing the shaft adjustable in 30 degree increments between horizontal and vertical orientations.
FIG. 3 is a partial front elevation of the left side of the apparatus cut away to show the left side input shaft and gear box, the shaft shown in a horizontal orientation.
FIGS. 4A, 4B, 4C, 4D and 4E is a perspective view of the group of grip styles consisting of A) knob handle, B) T-handle, C) pin handle, D) crank handle, and E) rim handle.

Left and right side rotatable input shafts are both positionally adjustable through an arc of about ninety degrees in thirty degree increments from a horizontal to a vertical orientation as depicted in FIG. 2. Both side rotatable input shafts are lockable in any of the four illustrated positions by respective left and right locking pins located beneath the left and right front rotatable input shafts, as illustrated by FIG. 3.

All four rotatable input shafts are configured to accept any of five or more types of interchangeable grips; a knob handle, a T-handle, a pin handle, a crank handle and a rim handle, as illustrated in FIG. 4. The input shafts are illustrated with knob handles throughout these drawings.

A rotatable drum is supported between the side plates and operated by a drum drive mechanism mounted on the outboard side of the right side plate. The right front and side rotatable shafts are coupled in a right side gearbox mounted on the outboard side of the right side plate. The right side gearbox output shaft connects to the drum drive mechanism, thus enabling right hand control of drum rotation, referred to elsewhere herein as vertical motion.

A bi-directional transversing assembly consisting of a stationary transverse beam located above, behind and parallel to the drum, a transversing yoke slidably fitted to the beam which confines sliding, rotatable targeting and stylus sectors in a fixed transverse relationship such that transversing movement of the yoke moves the sectors the same distance. The yoke is moved transversely by a drive belt over an idler wheel and drive wheel located at the back of the apparatus.

The left front and left side rotatable shafts are coupled in a left side gear box mounted on the outboard side of the left side plate. A left side gearbox output shaft connects to the drive wheel at the rear of the apparatus, thus enabling left hand control of the bi-directional transversing assembly, referred to elsewhere herein as transverse motion.

The right side of the drum is configured with a pattern holddown plate and registration pins so that printed patterns and other printed matter can be repeatedly reattached to the drum in the same location. Likewise, the left side of the drum has a trace holddown plate and registration pins so that trace records may be repeatedly attached in the same place on the left side of the drum and always be in the same geometric relationship to the materials on the right side of the drum.

A transverse index scale pointer and targeting image are suspended over the right side of the drum from an arm connected to the targeting sector. The arm and sector are rotatable up and back for installation of materials on the drum. A transverse index scale marked off in small but easily distinguishable units is attached to the deck plate on the right side and close to the drum so that the scale and pointer relationship can be easily viewed by the testing subject. Left hand control inputs will cause transverse motion resulting in the targeting image and pointer moving back and forth over the span of the scale.

A vertical index scale likewise marked off in small but easily distinguishable units is inscribed on right hand side of the drum or alternately printed on a test pattern and attached to the right side of the drum. A corresponding vertical index scale pointer is attached to the right side plate so that it extends out over the right edge of the drum where the scale and pointer relationship can be easily viewed by the testing subject.

In operation, the tester selects or designs a standard test pattern with vertical and transverse line components forming continuous line segments. The test pattern is registered and secured to the right side of the drum, and the targeting sector arm is rotated down into position over the test pattern so that the targeting image is superimposed on the pattern and in easy view of the testing subject.

A blank trace record is then registered and attached to the left side of the drum, and the stylus sector arm and marker is rotated down into position so that the marker is contacting the trace record.

The tester selects between using the front inputs and the side inputs. If side inputs are selected, then the rotatable side input shafts are adjusted to the desired orientation from horizontal to vertical in thirty degree increments as illustrated in FIG. 2, and locked in the selected position by respective left and right side locking pins on the front plate.

A grip style is selected from among the group consisting of knob handles, T-handles, pin handles, crank handles and rim handles, and the selected input shafts so configured.

The testing subject then grasps selected left and right hand controls and while viewing the targeting image superimposed over the test pattern, attempts to adjust the relative transverse and vertical positions to follow the test pattern with the targeting image. The resulting rotation of the drum and the transverse motion of the yoke and sectors makes a test trace on the trace record in the same orientation and to the same scale as the test pattern.

The test may or may not be timed. After the test, the pattern and trace are removed, the trace, which may be made on a transparent or semi-transparent material, can be laid over the test pattern for a direct evaluation of demonstrated coordination.

In a variation of the invention, the subject may be presented with either audio or visual instructions for plotting a pattern defined by several two-dimensional coordinates and connecting transverse and vertical line segments. With a trace record installed, and by raising and lowering the marker as necessary, the subject can manipulate the controls to position the transverse index scale pointer to its scale, and the vertical index scale to its pointer, to plot and connect the coordinates as instructed. The test may or may not be timed. The results are evaluated in the same manner as above.

Reference is now made to FIGS. 1–11 which illustrate pictorially the various elements of the preferred embodiment of the invention.

Figure 1:
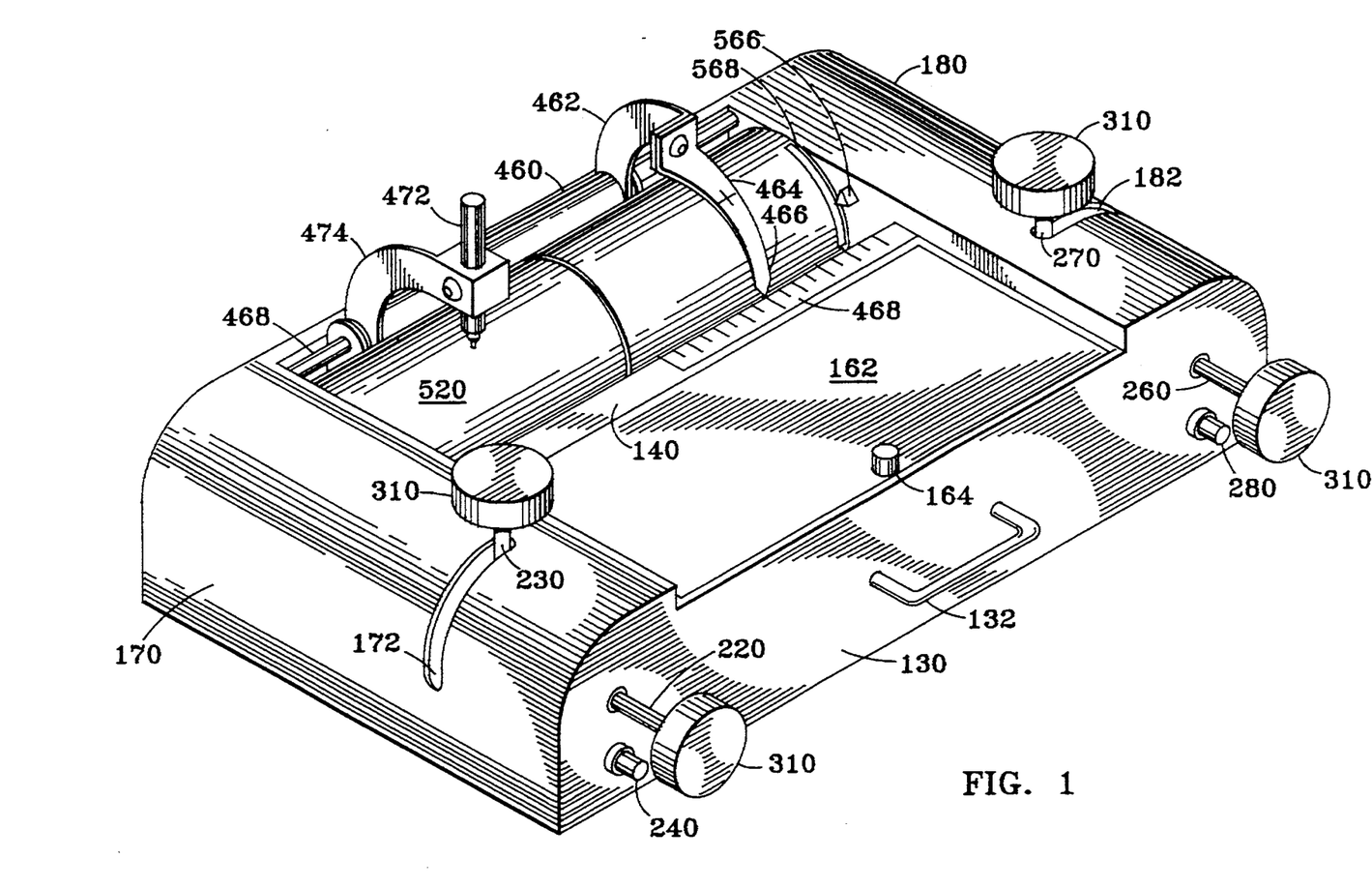
FIG. 1 is a left-front perspective view of the preferred embodiment.

Base plate 100 supports left side plate 110 and right side plate 120, to which is secured front plate 130 and deck plate 140, hence forming a storage area. Storage area lid 162 and lid fastener 164 are attached to deck plate 140. Handle 132 is secured to front plate 130.

Left side panel 170 with left side rotatable shaft slot 172 is secured to base plate 100 and left side plate 110. Right side panel 180 with right side rotatable shaft slot 182 is secured to base plate 100 and right side plate 120.

Left front rotatable shaft 220 and right front rotatable shaft 260 protrude from respective left and right sides of front plate 130. Both shafts are illustrated configured with knob handles 310.

Left side rotatable shaft 230 protrudes from left side rotatable shaft slot 172. Right side rotatable shaft 270 protrudes from right side rotatable shaft slot 182. Both shafts are illustrated configured with knob handles 310.

Left side rotatable shaft 230 and right side rotatable shaft 270 are both positionally adjustable through an arc of about ninety degrees in thirty degree increments from a horizontal to a vertical orientation as depicted in FIG. 2. Both side rotatable shafts are lockable in any of the four illustrated positions by respective left and right locking pins 240 and 280, which pins protrude from respective left and right sides of front plate 130.

All four rotatable shafts, 220, 230, 260 and 270 are configured to accept any of interchangeable grips; knob handle 310, T-handle 320, pin handle 330, crank handle 340 and rim handle 350.

Figures 7, 8:
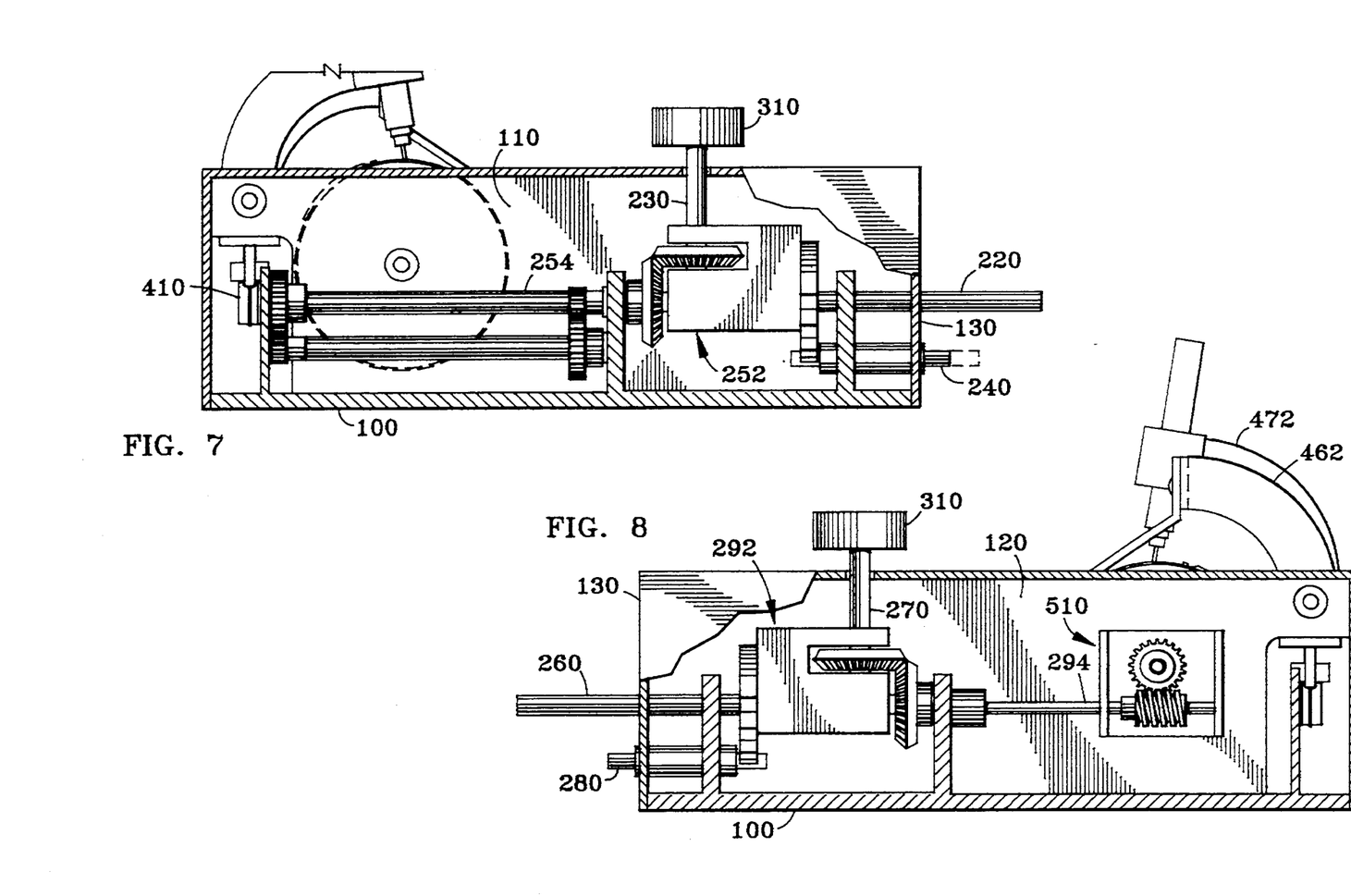
FIG. 7 is a left side elevation of the uncovered apparatus and exposed transverse gear train showing the left front rotatable shaft and the left side rotatable shaft adjusted to a vertical orientation, both coupled to the left side gear box, the gearbox output shaft terminating at the transversing assembly drive wheel.
FIG. 8 is a right side elevation of the uncovered apparatus and exposed vertical gear train showing the right front rotatable shaft and the right side rotatable shaft adjusted to a vertical orientation, both coupled to the right side gear box, the gearbox output shaft terminating in the drum drive mechanism.

Rotatable drum 520 is supported between left side plate 110 and right side plate 120, and operated by drum drive mechanism 510 mounted on the outboard side of right side plate 120. Right front and right side rotatable shafts 260 and 270 are coupled by right side gear box 292 which is mounted on the outboard side of right side plate 120. Right side gearbox output shaft 294 operates drum drive mechanism 510, thus enabling right hand control of drum rotation, referred elsewhere herein as vertical motion, by using either right front rotatable shaft 260 or right side rotatable shaft 270.

Figure 9:
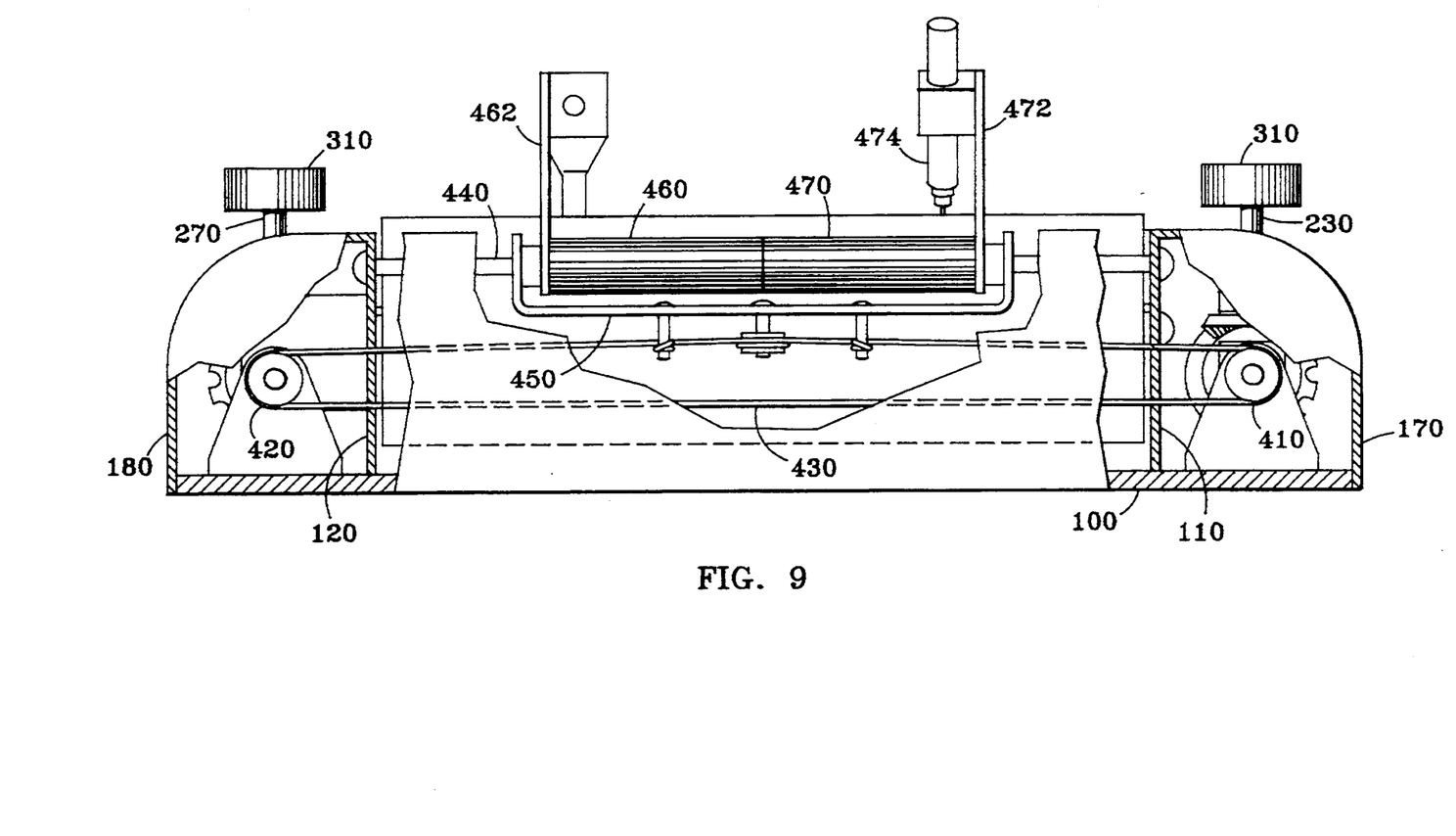
FIG. 9 is a rear elevation cut-away view of the apparatus and the bi-directional transversing assembly showing the drive wheel, idler wheel, drive belt, transversing yoke, targeting sector, stylus sector and transverse beam.

Transversing assembly 400 consists of a stationary transverse beam 440 located above, behind and parallel to drum 520, transversing yoke 450 slidably fitted to beam 440 and thereon confining slidably attached targeting sector 460 and slidably attached stylus sector 470 in a fixed transverse relationship such that transversing movement of yoke 450 moves sectors 460 and 470 together the same distance in the same direction at the same time. Yoke 440 is moved transversely by drive belt 430 over idler wheel 420 and drive wheel 410.

Left front and left side rotatable shafts 220 and 230 are coupled by left side gear box 252 which is mounted on the outboard side of left side plate 110. Left side gearbox output shaft 254 operates drive wheel 410, thus enabling left hand control of transversing assembly 400, referred elsewhere herein as transverse motion, by using either left front rotatable shaft 220 or left side rotatable shaft 230.

Figures 5, 6:
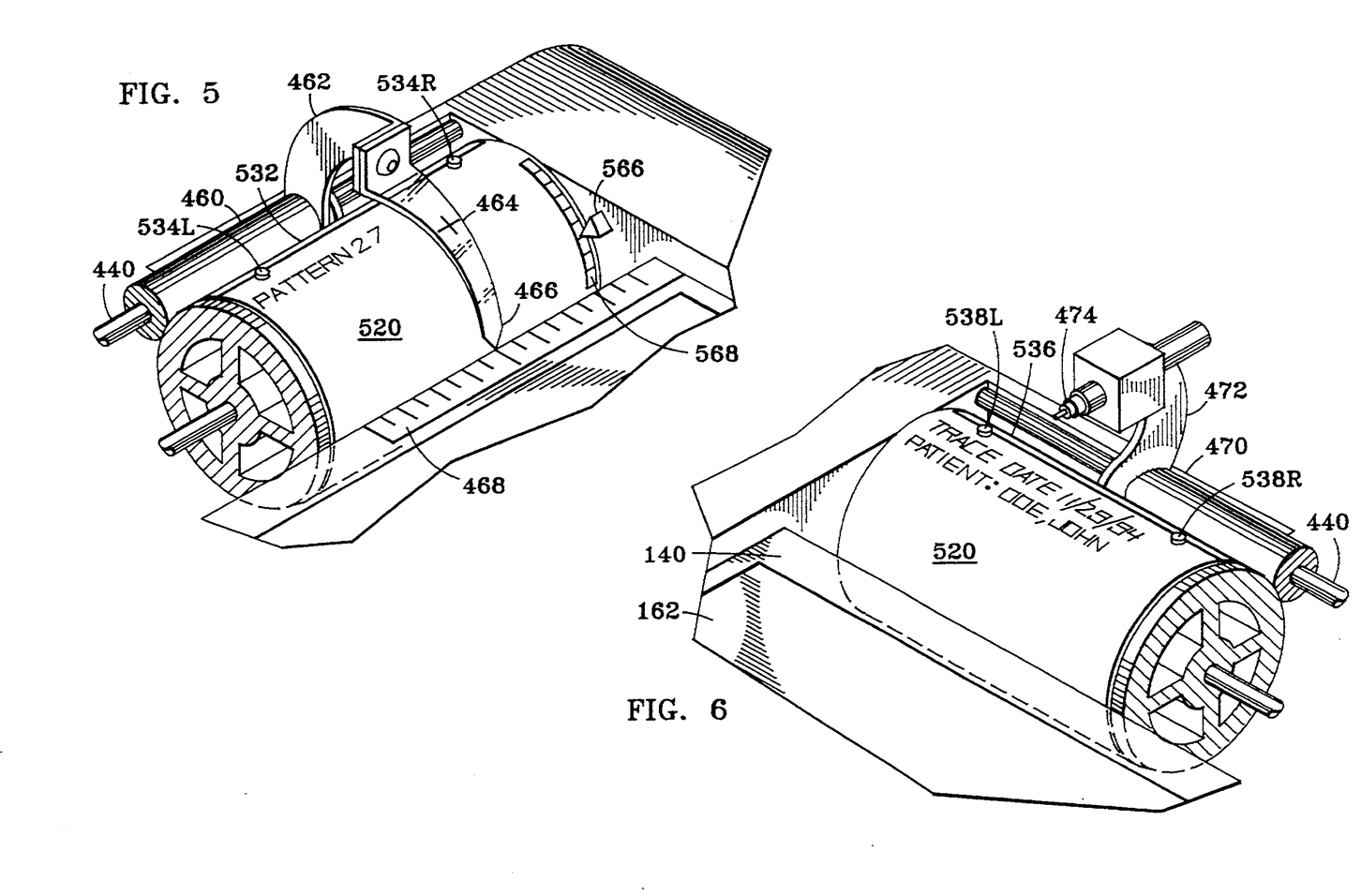
FIG. 5 is a close-up cut-away perspective showing the right side of the drum with pins for registering test patterns, the targeting sector on the transverse beam, targeting sector arm with targeting image and transverse index scale pointer, the transverse index scale on the deck in front of the drum, the vertical index scale at the right end of the drum and the vertical scale index pointer attached to the right side plate adjacent to the drum.
FIG. 6 is a close-up cut-away perspective showing the left side of the drum with pins for registering trace records, the stylus sector on the transverse beam, stylus sector arm and marker rotated up and back from the drum and trace record.

Right half of drum 520 is configured with a pattern holddown plate 532 and pattern registration pin pair 534, such that printed patterns and other printed matter may be repeatedly attached to drum 520 in the same location. Likewise, left side of drum 520 is configured with trace holddown plate 536 and trace registration pin pair 538, such that trace records may be repeatedly attached in the same place on the left side of drum 520 and always in the same geometric relationship to materials in register on the right side of drum 520.

Transverse index scale pointer 466 and targeting image 464 are suspended over right side of drum 520 by sector arm 462, which is rotatable up and back for installation of materials on drum 520. Transverse index scale 468 is secured to deck plate 140 on the right side and close to drum 520, such that scale 468 and pointer 466 relationship can be easily viewed from in front. Left hand inputs will cause transverse motion resulting in targeting image 464 and pointer 466 movements over the span of scale 468.

Vertical index scale 568 is inscribed on right hand side of drum 520 or alternately printed on a pattern and attached in uniform registration to drum 520. Vertical index scale pointer 566 is attached to right side plate 120 and protrudes out over drum 520 such that scale 568 and pointer 566 relationship can be easily viewed from in front.

Figure 10:
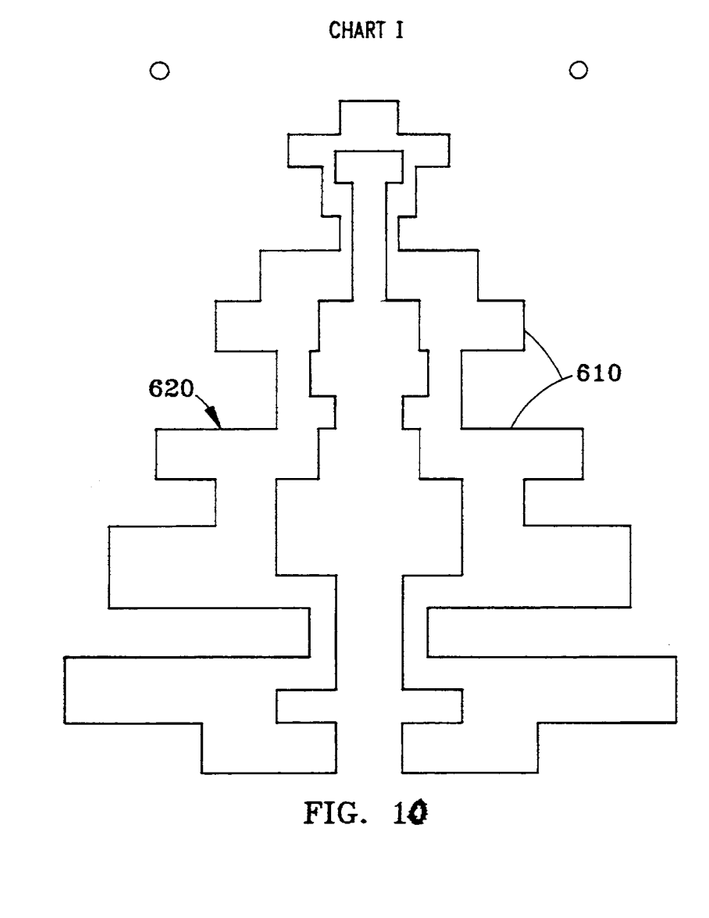
FIG. 10 is a typical test pattern of transverse and vertical line segments.

In operation, a standard test pattern 600 with vertical and transverse line components 610 forming continuous line segments 620 is attached by pattern holddown plate 532 on pattern registration pin pair 534, and targeting sector arm 462 is rotated down into position such that targeting image 464 is superimposed on test pattern 600 and in easy view of the testing subject.

Trace record 700 is attached by trace holddown plate 536 on trace registration pin pair 538 and stylus sector arm 472 is rotated down into position such that marker 474 is contacting trace record 700.

Selection is made between using front rotatable shafts; left 220 and right 260, or side rotatable shafts; left 230 and right 270. If side rotatable shafts 230 and 270 are selected, they are adjusted to a desired orientation from horizontal to vertical in thirty degree increments as illustrated in FIG. 2, and locked in the selected position by respective left and right side locking pins 240 and 280.

A grip style is selected from among the group consisting of knob handles 310, T-handles 320, pin handles 330, crank handles 340, and rim handles 350, and the selected rotatable shafts so configured.

Figure 11:
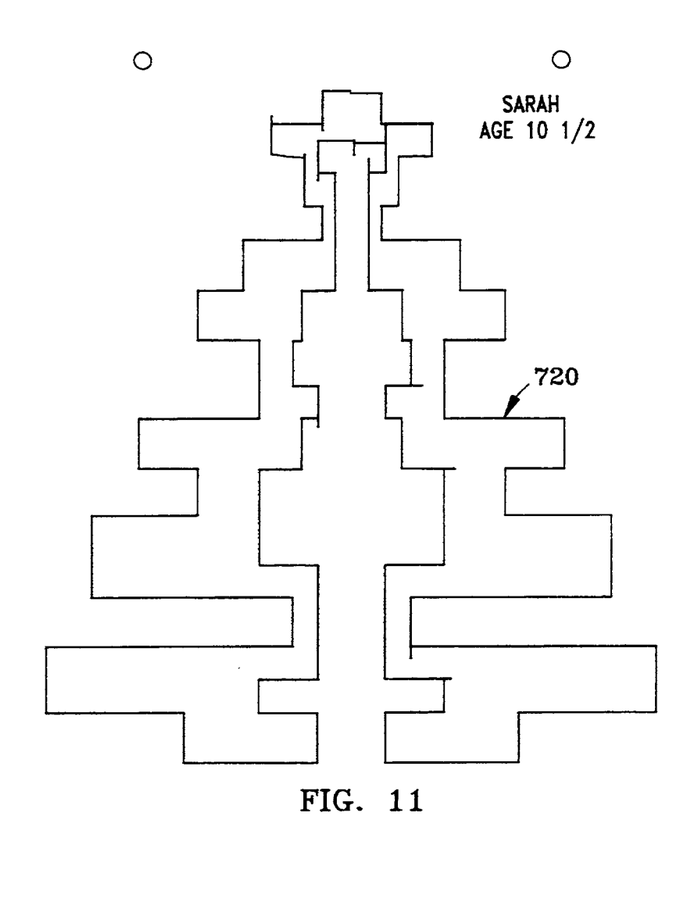
FIG. 11 is a typical permanent trace, representing the effort of the tested subject to traverse a test patten, the trace showing the same orientation and scale as the test pattern of FIG. 10.

The testing subject then grasps selected left and right hand controls and while viewing targeting image 464 superimposed over test pattern 600, attempts to adjust their relative transverse and vertical position with appropriate left and right inputs in order to follow line segment 620 with targeting image 464. The resulting bi-directional rotation of drum 520 and bi-directional transverse motion of transversing assembly 400 makes permanent trace 720 on trace record 700 in the same orientation and scale as test pattern line segment 620 on test pattern 600.

The test may or may not be timed. Upon completion of the test and removal from the drum, trace record 700 can be overlaid on test pattern 600 for a direct evaluation of demonstrated coordination.

In a variation of the invention, subject may be presented with audio or visual instructions for producing a pattern defined by several two-dimensional coordinates and connecting transverse and vertical line segments. With a blank trace record 700 installed, and by raising and lowering marker 474 as necessary, the person being tested may plot the coordinates by manipulating selected inputs to adjust relative position of transverse index scale 468 and respective pointer 466, and relative position of vertical index scale 568 and respective pointer 566, to mark and connect coordinates as instructed. The test may or may not be timed. A resulting trace is made and evaluated in the same manner as above.

I claim:

1. An apparatus for testing coordination comprising:
   means of presenting to a person a test pattern of at least two dimensions,
   means of presenting a targeting image superimposed over said test pattern,
   means of causing adjustment to relative position of said targeting image and said test pattern in said at least two dimensions, and
   means of making a permanent trace of said adjustments to said relative position of said targeting image and said test pattern,
   said permanent trace of said adjustments being in the same orientation and scale as said test pattern,
   said means of said causing said adjustments to said relative position comprising: left hand controls comprising a left side rotatable shaft positionally adjustable through an arc of about ninety degrees from a horizontal to a vertical orientation and a left front rotatable shaft, rotation of any said left hand control causing adjustment in said relative position of said targeting image and said test pattern in a first dimension; and right hand controls comprising a right side rotatable shaft positionally adjustable through an arc of about ninety degrees from a horizontal to a vertical orientation and a right front rotatable shaft, rotation of any said right hand control causing adjustment in said relative position of said targeting image and said test pattern in a second dimension,
   said rotatable shafts configurable with interchangeable grip styles from the group consisting of knob handle, T-handle, pin handle, crank handle and rim handle.

2. The apparatus of claim 1, further comprising means for adjusting resistance of said rotatable shafts to applied forces.

3. The apparatus of claim 1, further comprising means for adjusting turn ratios between said rotatable shafts and resultant amount of said adjustment of said relative position of said targeting image and said test pattern.

4. The apparatus of claim 1, further comprising:
   means for plotting a multiplicity of coordinates in at least two dimensions and creating line segments between selected said coordinates;
   means for making a permanent trace of said plotting and said creating.

5. The apparatus of claim 4, said means for said plotting said coordinates comprising: said left hand controls configured to cause said adjustments to said relative position of a transverse index scale and transverse index scale pointer in a transverse dimension; and said right hand controls configured to cause said adjustments to said relative position of and said relative position of a vertical index scale and vertical index scale pointer in a vertical dimension.

6. The apparatus of claim 1, said means of presenting comprising a drum of uniform circumference oriented and rotatable on a horizontal axis perpendicular to subject's line of sight, said drum configured to detachably accept said test pattern in uniform registration thereon;

said test pattern formed by a multiplicity of transverse and vertical line components connected to form at least one continuous line segment;

said means of making a permanent trace of said adjustments further comprising: said drum further configured to detachably accept a trace record in said uniform registration adjacent to said test pattern, a marker supported by a stylus sector arm of a stylus sector, said marker being in marking contact with said trace record, said stylus sector slidably affixed to a transverse beam behind and parallel to said drum, said stylus sector arm being manually rotatable up and away from said trace record;

said targeting image comprising cross hairs supported by a targeting sector arm of a targeting sector, said targeting image being said superimposed over installed said test pattern in line of sight of said subject, said targeting sector slidably affixed to said transverse beam behind and parallel to said drum, said targeting sector arm being manually rotatable up and away from said drum;

said left side and left front rotatable shafts coupled by a left side gear box, said left side gear box having an output shaft connected to a bi-directional transversing assembly, said transversing assembly comprising a transversing yoke slidably affixed to said transverse beam, said yoke confining said targeting sector and said stylus sector in a fixed transverse relationship such that said targeting image and said marker maintain a constant special relationship during transverse motion;

said right side and right front rotatable shafts coupled by a right side gear box, said right side gear box having an output shaft connected to a bi-directional drum drive mechanism and hence to said drum.

7. The apparatus of claim 6, said apparatus further comprising:

means for plotting a multiplicity of coordinates in at least two dimensions and creating line segments between selected said coordinates;

means for making a permanent trace of said plotting and said creating;

said means for said plotting said coordinates comprising said left hand controls configured to cause adjustments to said relative position of a transverse index scale and transverse index scale pointer in a transverse dimension, and said right hand controls configured to cause adjustment to said relative position of a vertical index scale and vertical index scale pointer in a vertical dimension;

said transverse index scale being attached in a stationary position at right front of and parallel to said drum, said transverse index scale pointer attached to said targeting arm sector and extending downwards towards said transverse index scale whereby range of transversing motion of said transverse said pointer is approximately equal to span of said transverse index scale;

said vertical index scale pointer attached in a stationary position to said apparatus at right side of said drum and protruding out into close proximity to said vertical index scale on said drum such that rotation of said drum changes said relative position of said vertical said pointer and said vertical index scale;

said left hand controls configured to cause adjustments to said relative position of said transverse index scale and said transverse index scale pointer and said right hand controls configured to cause adjustments to said relative position of said vertical index scale to said vertical scale index pointer.

\* \* \* \* \*